United States Patent
Maschio

(10) Patent No.: US 11,950,969 B2
(45) Date of Patent: Apr. 9, 2024

(54) TRACKING OF RETINAL TRACTION THROUGH DIGITAL IMAGE CORRELATION

(71) Applicant: ALCON INC., Fribourg (CH)

(72) Inventor: Niccolo Maschio, Zürich (CH)

(73) Assignee: Alcon Inc., Fribourg (CH)

( * ) Notice: Subject to any disclaimer, the term of this patent is extended or adjusted under 35 U.S.C. 154(b) by 422 days.

(21) Appl. No.: 17/490,456

(22) Filed: Sep. 30, 2021

(65) Prior Publication Data

US 2022/0265383 A1    Aug. 25, 2022

Related U.S. Application Data

(60) Provisional application No. 63/151,954, filed on Feb. 22, 2021.

(51) Int. Cl.
*A61B 90/00* (2016.01)
*A61B 3/12* (2006.01)
(Continued)

(52) U.S. Cl.
CPC ............ *A61B 90/37* (2016.02); *A61B 3/12* (2013.01); *G06T 7/285* (2017.01); *G16H 30/40* (2018.01);
(Continued)

(58) Field of Classification Search
CPC ...................................... A61B 90/00
See application file for complete search history.

(56) References Cited

U.S. PATENT DOCUMENTS

| 11,071,449 | B2 * | 7/2021 | Heeren | ............... | A61B 3/102 |
| 2014/0160264 | A1 | 6/2014 | Taylor et al. | | |
| 2021/0386285 | A1 * | 12/2021 | Walsh | ............... | A61B 5/0066 |

FOREIGN PATENT DOCUMENTS

| CN | 110537895 A | 12/2019 |
| JP | 2018068707 A | 5/2018 |

(Continued)

OTHER PUBLICATIONS

Brochan, A. Martina; Tappeiner, Christoph; Rothenbuehler, Simon P.; Rudolph, Tobias; Amstutz, Christoph A.; Kowal, Jens H. "Multimodal Registration Procedure for the Initial Spatial Alignment of a Retinal Video Sequence to a Retinal Composite Image" IEEE Transactions on Biomedical Engineering, vol. 57, No. 8, Aug. 2010.

*Primary Examiner* — Di Xiao
(74) *Attorney, Agent, or Firm* — Quinn IP Law

(57) ABSTRACT

A tracking system for quantifying retinal traction on a retina of a patient eye includes an indicator device, a stereo camera, and an electronic control unit (ECU). The stereo camera collects and outputs stereo image data. The ECU, which is in communication with the indicator device, executes a method by receiving the stereo image data from the stereo camera during an ophthalmic procedure and thereafter assigning tracking points as coinciding pixels within stereo image pairs. The ECU also automatically performs a digital image correlation (DIC) process using the stereo image pairs to ascertain relative motion of the tracking points, and associates relative motion of the tracking points with the retinal traction using a traction map. A numeric traction quotient is generated that is indicative of magnitude of retinal traction. The ECU executes a control action using the indicator device based on the numeric traction quotient.

20 Claims, 5 Drawing Sheets

(51) Int. Cl.
 *G06T 7/285* (2017.01)
 *G16H 30/40* (2018.01)
 *G16H 40/40* (2018.01)
 *G16H 40/63* (2018.01)
 *H04N 13/204* (2018.01)

(52) U.S. Cl.
 CPC ............ *G16H 40/40* (2018.01); *G16H 40/63* (2018.01); *H04N 13/204* (2018.05); *A61B 2090/371* (2016.02); *G06T 2207/30041* (2013.01)

(56) References Cited

FOREIGN PATENT DOCUMENTS

| WO | 2007110982 A1 | 10/2007 | |
|---|---|---|---|
| WO | WO-2020160097 A1 * | 8/2020 | ........... A61B 3/0033 |
| WO | 2020215361 A1 | 10/2020 | |

\* cited by examiner

TRACKING OF RETINAL TRACTION THROUGH DIGITAL IMAGE CORRELATION

CROSS-REFERENCE TO RELATED APPLICATIONS

This application claims priority to and the benefit of U.S. Patent Application Ser. No. 63/151,954 filed on Feb. 22, 2021, which is incorporated herein by reference in its entirety.

TECHNICAL FIELD

The present disclosure relates to an imaging-based strategy for quantifying, tracking, and mitigating tractive forces on a retina during retinal surgery.

BACKGROUND

Vitrectomy and other invasive surgeries of the eye require a surgeon to insert specialized surgical tools into the vitreous cavity of a patient's eyeball, and to thereafter manipulate the surgical tools when performing a particular surgical technique. The surgeon's actions are guided in real-time by highly magnified imagery of the retina and surrounding intraocular tissue. To this end, magnified retinal images are typically displayed within view of the surgeon and other attending clinicians. At the same time, the magnified retina may be viewed in other ways, such as through eye pieces of a high-power ophthalmic microscope.

As appreciated in the art, the vitreous cavity extends between the lens and the retina of the human eye, with the lens and the retina being respectively located at the anterior region and the posterior region of the eyeball. The vitreous cavity is occupied by a transparent, gel-like substance referred to as the vitreous humor, which itself is encapsulated within a thin membrane called the vitreous cortex. The retina is isolated from the vitreous body by another thin intervening layer of tissue, i.e., the inner limiting membrane or ILM.

Due to adherence of the ILM to the retinal surface, common ophthalmic surgeries such as the repair of macular holes or torn retinas, removal of scar tissue, and other delicate surgeries of the eye may require the attending surgeon to securely grasp and carefully peel the ILM away from the backing retina. ILM peeling has the effect of relaxing the disturbed retina, while also providing the surgeon with unimpeded access to the retinal surface. Performance of an ILM peeling procedure involves the deliberate application of surgeon-imparted tractive forces to the ILM. As the surgeon maneuvers the ILM away from the retina, such forces are transferred to the attached retina. The resulting traction across the retinal surface is referred to herein and in the general art as retinal traction.

SUMMARY

Disclosed herein are automated imaging-based systems and methods for quantifying retinal traction during the performance of an ophthalmic procedure, principally but not necessarily limited to vitrectomy and other invasive eye surgeries. As appreciated in the art, alternative approaches for manipulating the inner limiting membrane (ILM) include a forceps-assisted "pinch-and-peel" technique and a friction-based technique, the latter of which utilizes a specialized scraping loop, e.g., the FINESSE™ Flex Loop Curved Nitinol loop commercially from Alcon, Inc. Use of both exemplary tools results in retinal traction, which may at times may lead to iatrogenic tearing of the ILM and other possible eye trauma.

ILM structural integrity for a given patient eye tends to vary due to factors such as heredity, age, injury, and disease. As a result, the effect of a particular magnitude and duration of applied retinal traction on a given patient eye is difficult to predict. Likewise, variations in surgeon skill level, intrinsic capabilities and limitations of the surgical tools employed by a given surgeon, and other factors can produce widely different end results. The present solutions are therefore intended to reduce uncertainty during retinal surgeries, while at the same time improving surgical outcomes and increasing overall surgeon confidence.

In order to accomplish these and other possible goals, the present approach relies on collection and processing of stereo images of the retina, along with an automated and/or surgeon-directed assignment of target pixels ("tracking points") as coinciding pixels within stereo image pairs of the stereo image data. Relative motion of the assigned tracking points is closely monitored during the ophthalmic procedure using an electronic control unit (ECU), e.g., a standalone or distributed computer device, or associated hardware integrated partially or fully with a stereo camera in different embodiments.

The ECU described herein uses a traction model to automatically quantify retinal traction, with the ECU ultimately outputting a numeric traction quotient indicative of a magnitude of such retinal traction. In a simplified approach, the numeric traction quotient may be a unitless value indicative of the magnitude, e.g., a normalized value having a maximum value of 1 and a minimum value of 0. The ECU automatically alerts the surgeon in real-time based on the numeric traction quotient, such as when the numeric traction quotient, possibly averaged across the entire surface area of the retina or within designated zones or regions thereof, exceeds a corresponding traction threshold. Real-time audio, visual, and/or tactile alerts may be generated in some embodiments to enable the surgeon to make more informed adjustments to tugging or pulling forces imparted by the surgeon to the ILM.

In a non-limiting exemplary embodiment, a tracking system for quantifying such retinal traction during an ophthalmic procedure includes an indicator device, a stereo camera, and an ECU. The ECU, which is in wired or wireless communication with the indicator device in this particular embodiment, is configured to receive stereo image data from the stereo camera, with the ECU possibly integrated with the stereo camera or existing as separate hardware in communication therewith. The controller thereafter assigns target pixels within the stereo image pairs, autonomously or using surgeon-directed input signals, with such assigned target pixels hereinafter referred to as "tracking points" for simplicity and clarity.

The ECU in this representative configuration is programmed with the above-noted traction model. While various approaches could be used to implement the envisioned traction model, one possible solution includes a software-based logic block configured to automatically perform a digital image correlation (DIC) process to the collected stereo images, with the DIC process used to ascertain relative motion of the tracking points. The ECU then associates the relative motion of the tracking points with the particular retinal traction causing such motion to occur, e.g., using a lookup table, with the ECU thereafter outputting the above-noted numeric traction quotient. The provided numeric traction quotient is thus indicative of the magnitude of the retinal traction as noted above. The ECU then executes an appropriate control action with respect to the indicator device based on the numeric traction quotient, for instance when the magnitude of the numeric traction quotient exceeds a pre-calibrated threshold or a user-calibratable threshold.

In order to ensure that the relative motion tracked by the ECU results principally from retinal traction applied by the surgeon, as opposed to baseline motion caused by other forces such as patient-induced and/or externally-induced eye motion, the ECU may be configured to apply a free-body/solid-body motion filter to the relative motion to account for and ultimately filter out such baseline motion.

The indicator device may include one or more high-resolution display screens, for instance 4K or higher resolution LED-backlit medical-grade monitors. In such an embodiment, the ECU may be configured to automatically present an intuitive "heat map" of the retinal surface via the display screen(s), alone or in conjunction with text messages or prompts. The displayed heat map, which is graphically representative of the present level of retinal traction, may pinpoint locations of relatively high traction in some configurations, e.g., on a pixel-by-pixel basis or a region-by-region basis. Such a heat map could be displayed on top of a displayed stereo image of the retina, such as in the form of an overlay to a three-dimensional fundus image, to indicate corresponding high-traction zones.

An accompanying method is also disclosed for quantifying retinal traction during an ophthalmic procedure. According to an exemplary embodiment, the method includes receiving the stereo image data from the stereo camera via the ECU during an ophthalmic procedure, with the stereo image data including a stereo image pair. The method also includes assigning tracking points as coinciding pixels within the stereo image pair, and automatically performing a DIC process, via the ECU, using the stereo image pair. In this manner the ECU ascertains relative motion of the tracking points.

Furthermore, the method in this particular embodiment includes associating relative motion of the tracking points with the retinal traction, using a traction map of the ECU, to thereby determine a numeric traction quotient indicative of magnitude of the retinal traction. The ECU thereafter executes a control action using the indicator device, with the control action being based on the numeric traction quotient and indicative of the magnitude of the retinal traction.

A system is also disclosed herein for quantifying retinal traction on a retina of a patient eye, with the system including a central processing unit (CPU) and computer-readable media on which is recorded a set of instructions. Execution of the instructions by the CPU causes the CPU to receive stereo image data, inclusive of a stereo image pair or pairs, from a stereo camera during the ophthalmic procedure, and to assign tracking points as coinciding pixels within the stereo image pair(s). The CPU also automatically performs a DIC process using the stereo images to ascertain relative motion of the tracking points. In this particular embodiment, the CPU associates relative motion of the tracking points with the retinal traction, using a traction map, as a numeric traction quotient indicative of magnitude of the retinal traction. The CPU thereafter communicates a control signal to an external indicator device when the numeric traction quotient exceeds one or more calibrated traction thresholds.

The above-described features and advantages and other possible features and advantages of the present disclosure will be apparent from the following detailed description of the best modes for carrying out the disclosure when taken in connection with the accompanying drawings.

Figure 1:
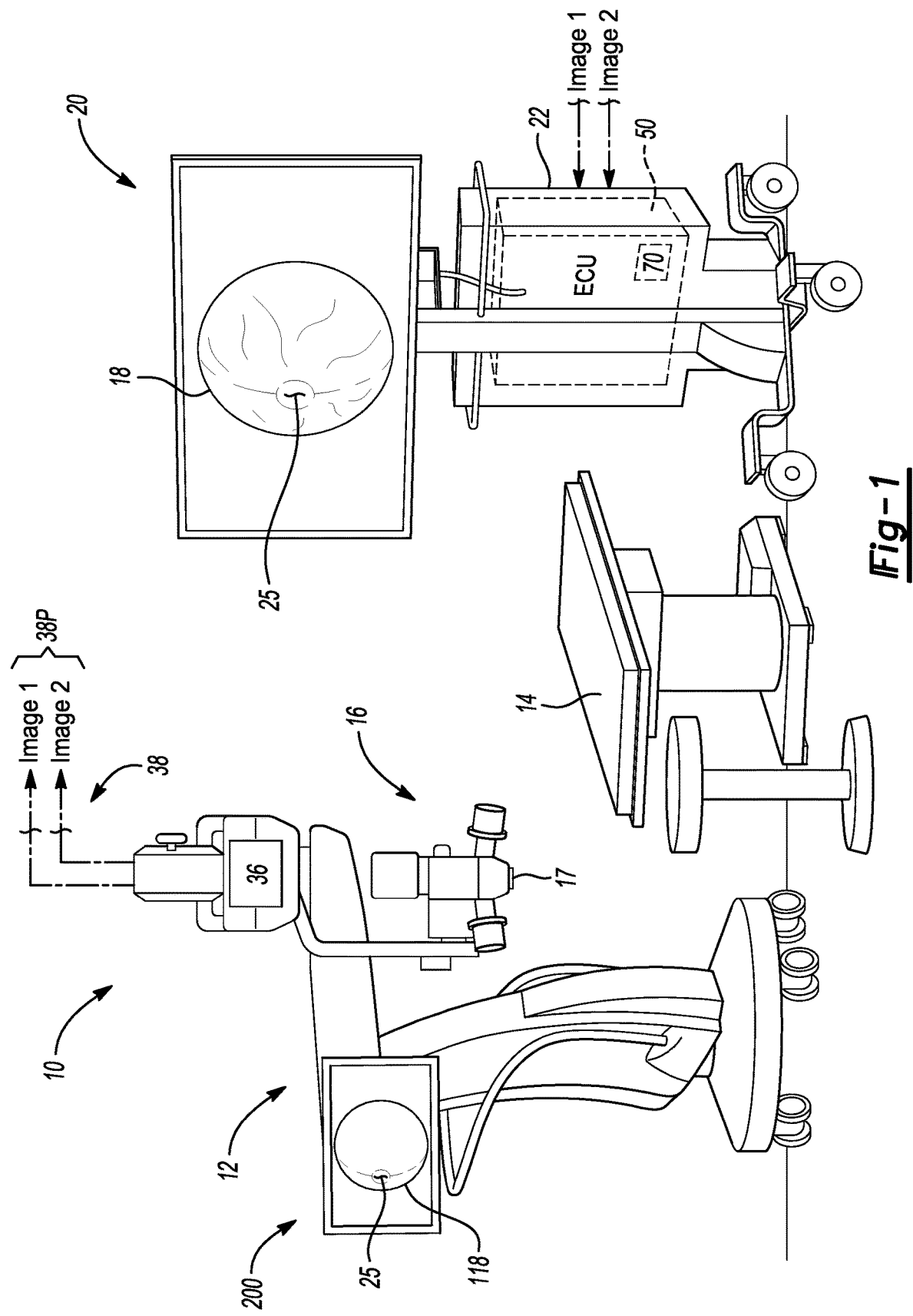
FIG. 1 is a schematic illustration of an operating room setup using a tracking system for automatically quantifying and tracking retinal traction during a representative ophthalmic procedure using a digital image correlation (DIC) process.

The foregoing and other features of the present disclosure are more fully apparent from the following description and appended claims, taken in conjunction with the accompanying drawings.

DETAILED DESCRIPTION

Embodiments of the present disclosure are described herein. It is to be understood, however, that the disclosed embodiments are merely examples and other embodiments can take various and alternative forms. The figures are not necessarily to scale. Some features could be exaggerated or minimized to show details of particular components. Therefore, specific structural and functional details disclosed herein are not to be interpreted as limiting, but merely as a representative basis for teaching one skilled in the art to variously employ the present disclosure. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Certain terminology may be used in the following description for the purpose of reference only, and thus are not intended to be limiting. For example, terms such as "above" and "below" refer to directions in the drawings to which reference is made. Terms such as "front," "back," "fore," "aft," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Figure 3:
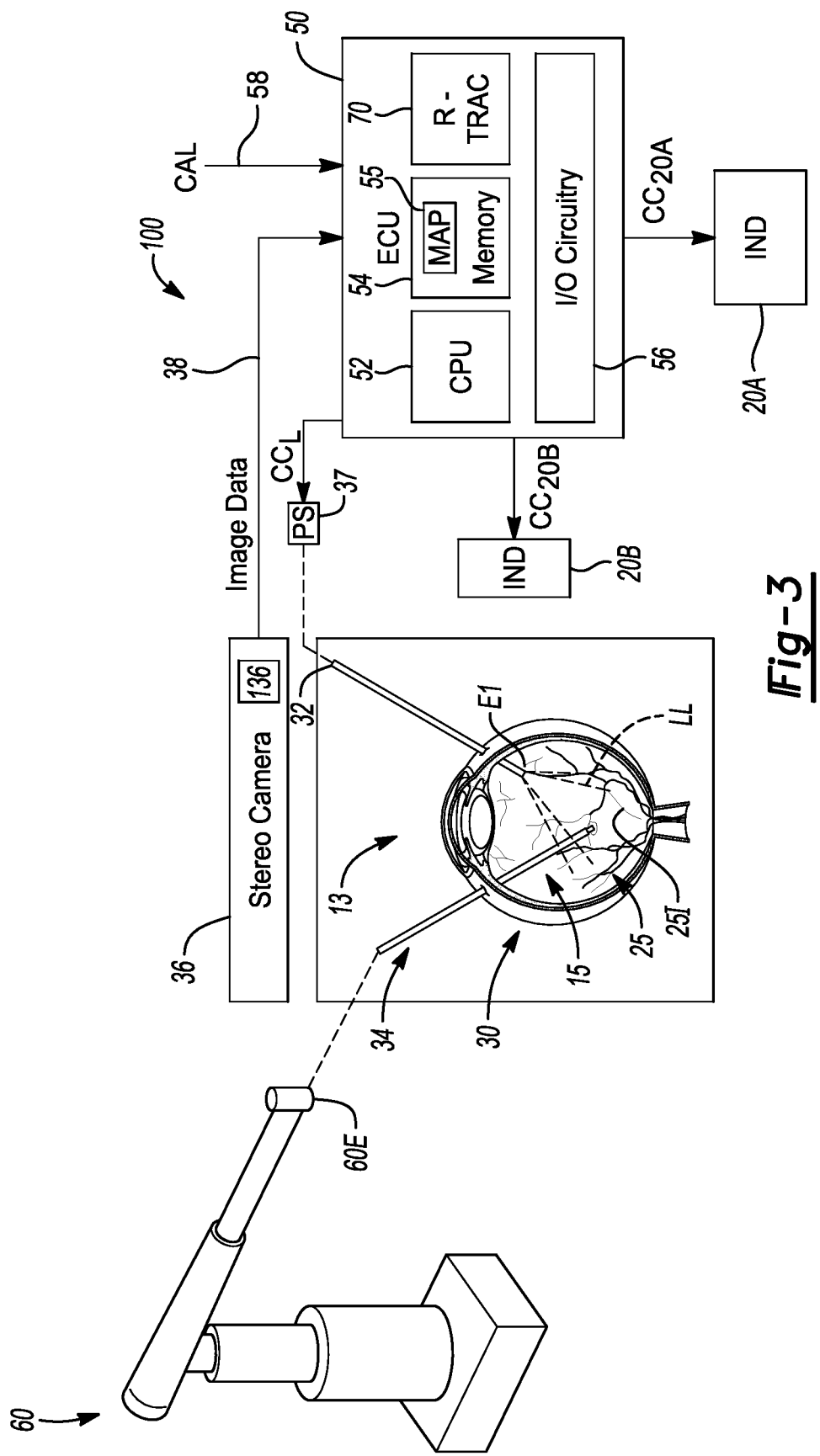
FIG. 3 is an exemplary embodiment of the tracking system shown in FIG. 1.

Referring to the drawings, wherein like reference numbers refer to like components, a representative surgical suite 10 is depicted schematically in FIG. 1. Such a surgical suite 10 may be equipped with a multi-axis surgical robot 12 and an operating platform 14, e.g., a table as shown or an adjustable/reclinable surgical chair. When the surgical suite 10 is occupied by a surgical team (not shown), the multi-axis surgical robot 12 may be connected to a stereo camera 16 through which a patient's intraocular anatomy may be visualized in three dimensions under high magnification, as appreciated in the art. Using associated hardware and software, a surgeon, in a heads-up manner using three-dimensional (3D) viewing glasses (not shown), is able to accurately visualize targeted tissue using highly magnified 3D images 18 and 118 of a retina 25 and surrounding anatomy, which may be displayed or projected using corresponding high-resolution medical display screens 20 and/or 200. Such display screens 20 and 200 are one possible embodiment of an indicator device (IND) 20A as shown in FIG. 3, enabling heads up viewing by the surgeon. Heads up viewing in this manner has the benefit of reducing stress and strain on the surgeon's neck and back relative to conventional top-down viewing of targeted tissue through eye pieces of an ophthalmic microscope.

The stereo camera 16, which may be configured as shown in the exemplary embodiment of FIG. 1 or in various other application-suitable sizes and/or shapes, includes or is communicatively connected to local control processor (LCP) 36. The LCP 36 may be embodied as a microprocessor, an application-specific integrated circuit (ASIC), central processor unit, etc., and is configured to collect and output stereo image data 38. That is, for each instant in time according to a predetermined sampling interval, two digital images are concurrently collected as stereo image pair 38P (Image 1, Image 2). As appreciated in the art, when the stereo image pair 38P is viewed by the surgeon and other attending clinicians through 3D glasses, the stereo image pair 38P converges into a 3D image.

Surgically useful levels of optical and/or digital magnification, and digital imaging of the retina 25 and other intraocular anatomy, is enabled by the ever-evolving capabilities of modern ophthalmic/surgical quality optical devices. The stereo camera 16 is one such device. The real-time availability of the stereo image data 38 from the stereo camera 16 during vitrectomy or other ophthalmic procedures is thus an enabling technology for the present solution described below with reference to FIGS. 2-6. Relative to approaches using a conventional ophthalmic microscope, during which the surgeon views the retina 25 through optical eye pieces throughout the surgery, the present solution allows the surgeon to maintain a more ergonomically friendly "heads up" posture, thus reducing stress and strain on the surgeon's neck and back.

Also present within the exemplary surgical suite 10 of FIG. 1 is a cabinet 22 containing an electronic control unit (ECU) 50 in communication with the indicator device 20A of FIG. 3. In different possible implementations, computer-readable instructions embodying a method 70, exemplified in FIG. 6, may reside aboard the ECU 50. The ECU 50 in turn may be a standalone computer as show in FIG. 1, a distributed/networked system, or partially or fully integrated with the stereo camera 16. The cabinet 22, depicted in an optional location as being collocated with the display screen 20, may be positioned elsewhere in the surgical suite 10.

Such a cabinet 22 may be constructed of a lightweight and easily sanitized construction, such as painted aluminum or stainless steel, and used to protect constituent hardware from possible ingress of dust, debris, and moisture. For improved visibility, light may be emitted by a lamp 17 mounted to an optical head of the stereo camera 16, and possibly from an endoilluminator 32 inserted into the patient's eye 30 of FIG. 3.

The ECU 50 of FIG. 1 is configured to receive the stereo image data 38, i.e., sequential stereo image pairs 38P represented schematically by arrows Image 1 and Image 2, with the ECU 50 receiving such stereo image data 38 from the stereo camera 16 in real-time. As part of the method 70, the ECU 50 assigns tracking points as coinciding pixels within the stereo image pair 38P, autonomously or with the involvement of the surgeon, and then automatically performs a digital image correlation (DIC) process on the stereo image pairs 38P to ascertain relative motion of the tracking points. Additionally, the ECU 50 associates relative motion of the tracking points with the retinal traction, such as by using a traction map 55 as depicted in FIG. 3, with the ECU 50 doing so as a numeric traction quotient indicative of magnitude of the retinal traction. The ECU 50 then executes a control action with respect to the indicator device(s) 20A and/or 20B of FIG. 3 and/or other audio, visual, or tactile devices based on the numeric traction quotient.

Figure 2:
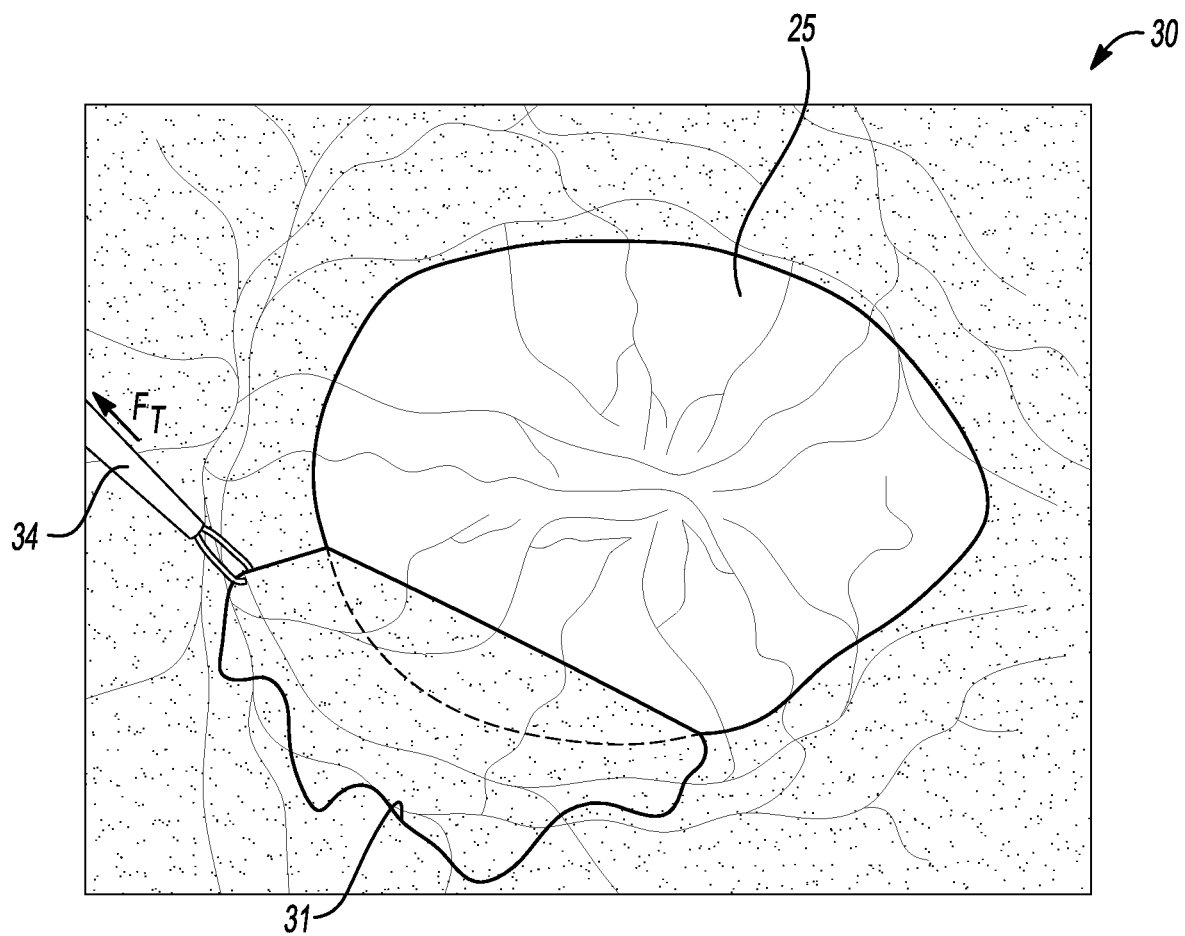
FIG. 2 is a schematic depiction of a representative ophthalmic procedure in which an inner limiting membrane (ILM) is grasped and peeled away from a retina, thereby imparting traction forces to the retina.

Referring briefly to FIG. 2, a representative patient eye 30 is shown undergoing an inner limiting membrane (ILM) peeling procedure in which an ILM 31 is carefully separated and peeled away from the backing retina 25 using a surgical tool 34. To accomplish the ILM peel, the surgeon carefully manipulates the surgical tool 34 to impart traction forces (arrow FT) to the ILM 31. In this manner, the surgeon is able to expose the retina 25 in preparation for work thereon. In actual practice the ILM 31, being thin, flexible, and transparent, is not easily identifiable. It is therefore common practice for the surgeon to apply a small amount of contrast-enhancing staining dye to the ILM 31, such as indocyanine green (ICG) or Membrane-Blue-Dual (DORC International), to lightly stain the ILM 31 and thereby improve contrast. With visualization of the ILM 31 enhanced in this manner, the surgeon may commence peeling the ILM 31 to expose the retina 25, as appreciated in the art.

As noted above, the structural integrity of the ILM 31 of a given patient is expected to vary, possibly quite widely, due to factors such as heredity, age, injury, and disease. The effects of retinal traction during a particular surgical instance are therefore difficult to predict absent the present teachings. Likewise, variations in surgical skill and the intrinsic capabilities and particular choice of surgical tools can collectively produce different surgical results over time. The present solutions are therefore intended to facilitate real-time monitoring of retinal traction during ILM peeling and other procedures, while also providing the surgeon with real-time intuitive feedback. Together, the monitoring and intuitive feedback allow the surgeon, whether working alone or with the assistance of the exemplary surgical robot 60 of FIG. 3, to make any necessary adjustments for optimal surgical results.

Referring now to FIG. 3, the patient eye 30 is shown undergoing a representative ophthalmic procedure 13, in this instance an invasive vitreoretinal surgery, during operation of a tracking system 100 constructed as set forth in detail herein. The tracking system 100 is operable for quantifying retinal traction within the patient eye 30. To this end, the tracking system 100 includes the indicator devices 20A and 20B, the stereo camera 16, and the ECU 50, the latter two of which may be integrated into a unitary device in some embodiments. During the course of the ophthalmic procedure 13, the endoilluminator 32 may be inserted into a vitreous cavity 15 of the patient eye 30. Light LL emitted from a distal end E1 of the endoilluminator 32, as well as some light from the lamp 17 of FIG. 1, is used to illuminate the vitreous cavity 15. Various lighting technologies may be used to emit the light LL, such as but not limited to red/green/blue (RGB) lasers, light-emitting diodes (LEDs), halogen bulbs, etc.

During the representative ophthalmic procedure 13 of FIG. 3, the surgeon may be required to insert the surgical tool 34 into the vitreous cavity 15 in order to perform an operating task on or in proximity to the retina 25. As appreciated by those skilled in the art, traditional approaches for manipulating the ILM 31 shown in FIG. 2 include a forceps-assisted "pinch-and-peel" technique, or the alternative use of a specialized scraping tool, such as the FINESSE™ Flex Loop Curved Nitinol loop from Alcon, Inc. Thus, the surgical tool 34 within the scope of the present disclosure may encompass either or both devices.

The above techniques are typically performed manually using the dexterous skill of the surgeon to manipulate the surgical tool 34. However, evolving machine vision-assisted robotic surgical techniques enable construction in some embodiments of a semi-automated or automated peeling procedure, e.g., using a multi-axis surgical robot 60. For instance, the surgical tool 34 could be attached to an end-effector 60E of the surgical robot 60, which in turn may be placed in communication with the ECU 50. Such a surgical robot 60 could be teleoperated by the surgeon through interaction with the ECU 50, either directly or via a human-machine interface (not shown) such as a surgical workstation. Alternatively, the surgical robot 60 could have limited support functionality, such as by offloading stress from the surgeon by supporting the weight of the surgical tool 34, reducing instances of tremors, etc., while leaving manipulation actions solely to the surgeon. Such automated peeling techniques, executed or supported to some extent by the surgical robot 60, would require in-depth knowledge of retinal traction, such as when measuring a retina indentation force as appreciated in the art.

With respect to the endoilluminator 32, the directed light LL falls incident upon exposed surfaces of the retina 25 to produce an illuminated retina surface 251, inclusive of the ILM 31 of FIG. 2, which is attached to the retina 25. The endoilluminator 32 is coupled to an accompanying power supply (PS) 37, controllable via a lighting control signals (arrow CCL) from the ECU 50 or another control processor, such as a filtered wall outlet or a battery pack and power inverter suitable for ensuring reliable generation and transmission of the directed light (arrow LL). During the course of the ophthalmic procedure 13, the stereo camera 16 collects the stereo image data 38 of the illuminated retina surface 251 and ILM 31 (FIG. 2), and thereafter transmits the collected stereo image data 38 to the ECU 50 for processing in accordance with the present retinal traction (R-TRAC) method 70.

The indicator device (IND) 20A, e.g., the display screens 20 and/or 200 of FIG. 1, is likewise in communication with the ECU 50, and configured to activate/turn on in response to an indicator control signal (arrow $CC_{20A}$) from the ECU 50. In response to the indicator control signal (arrow $CC_{20A}$), and depending on the particular configuration of the indicator device 20A, the indicator device 20A may provide a suitable visual alarm, such as the heat map 45 shown in FIG. 4 and described below. The ECU 50 thus uses the indicator device 20A to present an intuitive graphical depiction of retinal traction levels relative to the surface area of the retina 25.

Another similarly configured indicator device 20B may be used in conjunction with the indicator device 20A to provide multiple alerts, perhaps escalating alerts in response to results of the method 70. For instance, the indicator device 20B may provide audio, visual, and/or tactile alarms or warnings. A possible implementation of the indicator device 20B is that of an audio speaker, in which case an indicator control signal (arrow $CC_{20B}$) may cause the indicator device 20B to sound an audible chime or warning tone. Alternatively, the indicator device 20B may include a color-coded lamp, such that receipt of the indicator control signal (arrow $CC_{20B}$) causes the indicator device 20B to light up in a readily identifiable manner, e.g., using red light. Tactile feedback such as low-level vibration may be presented to the surgeon or another clinician in the surgical suite 10 of FIG. 1, with possibilities including a wearable device, floor mat, etc.

Although the ECU 50 of FIG. 3 is depicted schematically as a unitary box for illustrative clarity and simplicity, the ECU 50 could include one or more networked devices each with a central processing unit (CPU) 52 and sufficient amounts of memory 54, i.e., computer-readable media, including a non-transitory (e.g., tangible) medium that participates in providing data/instructions that may be read by the CPU 52. Instructions embodying the method 70 and the accompanying traction map 55 may be stored in memory 54 and executed by the CPU 52 to cause the CPU 52 to perform the various functions described herein, thus enabling the present method 70, possibly in conjunction with calibratable inputs 58 (arrow CAL).

The memory 54 may take many forms, including but not limited to non-volatile media and volatile media. As understood in the art, non-volatile media may include optical and/or magnetic disks or other persistent memory, while volatile media may include dynamic random-access memory (DRAM), static RAM (SRAM), etc., any or all which may constitute a main memory of the ECU 50. Input/output (I/O) circuitry 56 may be used to facilitate connection to and communication with the various peripheral devices used during the ophthalmic procedure 13, inclusive of the stereo camera 16, the endoilluminator 32, and the indicator devices 20A and/or 20B. Other hardware not depicted but commonly used in the art may be included as part of the ECU 50, including but not limited to a local oscillator or high-speed clock, signal buffers, filters, etc.

Figure 4:
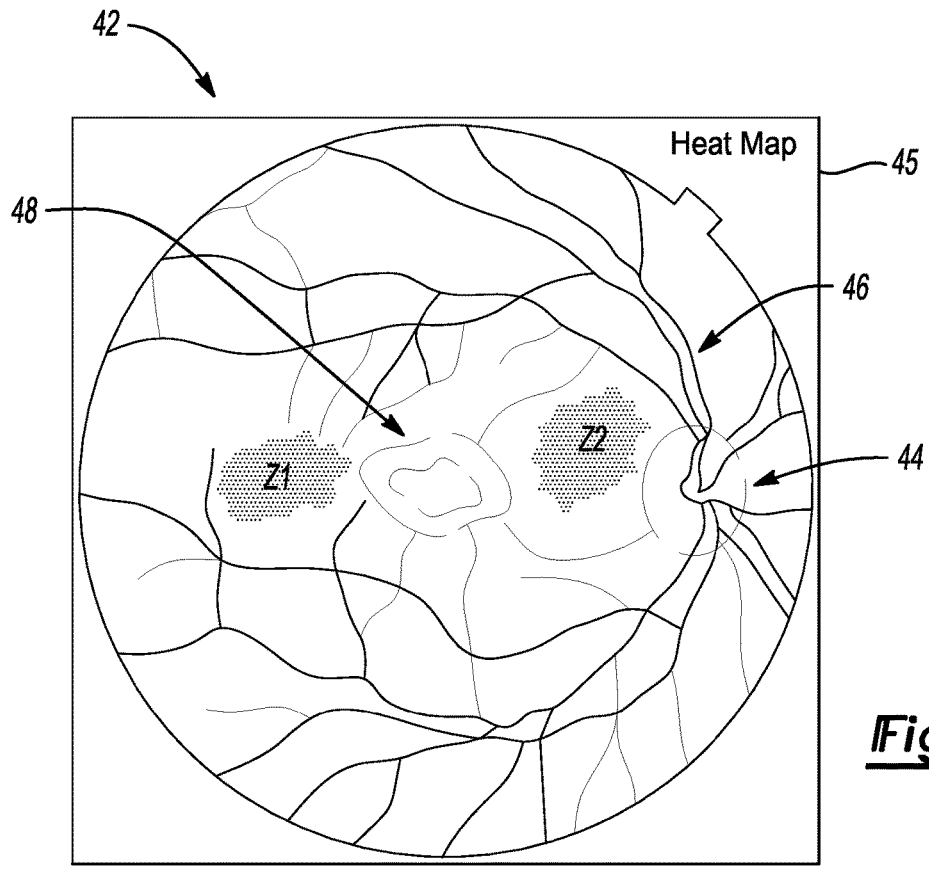
FIG. 4 is a schematic illustration of a heat map depicting areas or zones of elevated retinal traction in accordance with an aspect of the disclosure.

Referring briefly to FIG. 4, the retina 25 is shown as a representative fundus image 42. As appreciated in the art, the fundus image 42 is typically embodied as a color, black and white, or grayscale image of various key structure of the retina 25, primarily the optic disc 44, the retinal artery 46 and surrounding veins stemming therefrom, and the macula 48. The fundus image 42, being ubiquitous in ophthalmic practice and thus familiar to attending clinicians, may be used as an intuitive backdrop to the displayed heat map 45. In such a configuration, the ECU 50 may be configured to digitally divide or otherwise separate the retina 25 into multiple virtual zones, with two such zones Z1 and Z2 depicted in FIG. 4, and to map retinal traction to the retina surface 25. In this manner, the multiple zones may have a corresponding level of retinal traction that could be separately diagnosed and responded to as an alternative to, e.g., averaging retinal traction across the entire surface area of the retina 25 and applying a single traction threshold.

In the optional display configuration of FIG. 4, the ECU 50 could overlay the heat map 45 onto the fundus image 42, i.e., a stereo image formed by the stereo image pair 38P of FIG. 1, with this information presented in real-time via the indicator device(s) 20A and/or 20B. The heat map 45 thus intuitively provides information that, at a glance, is indicative of a distribution or concentration of a magnitude of retinal traction across the retina 25.

Figure 6:
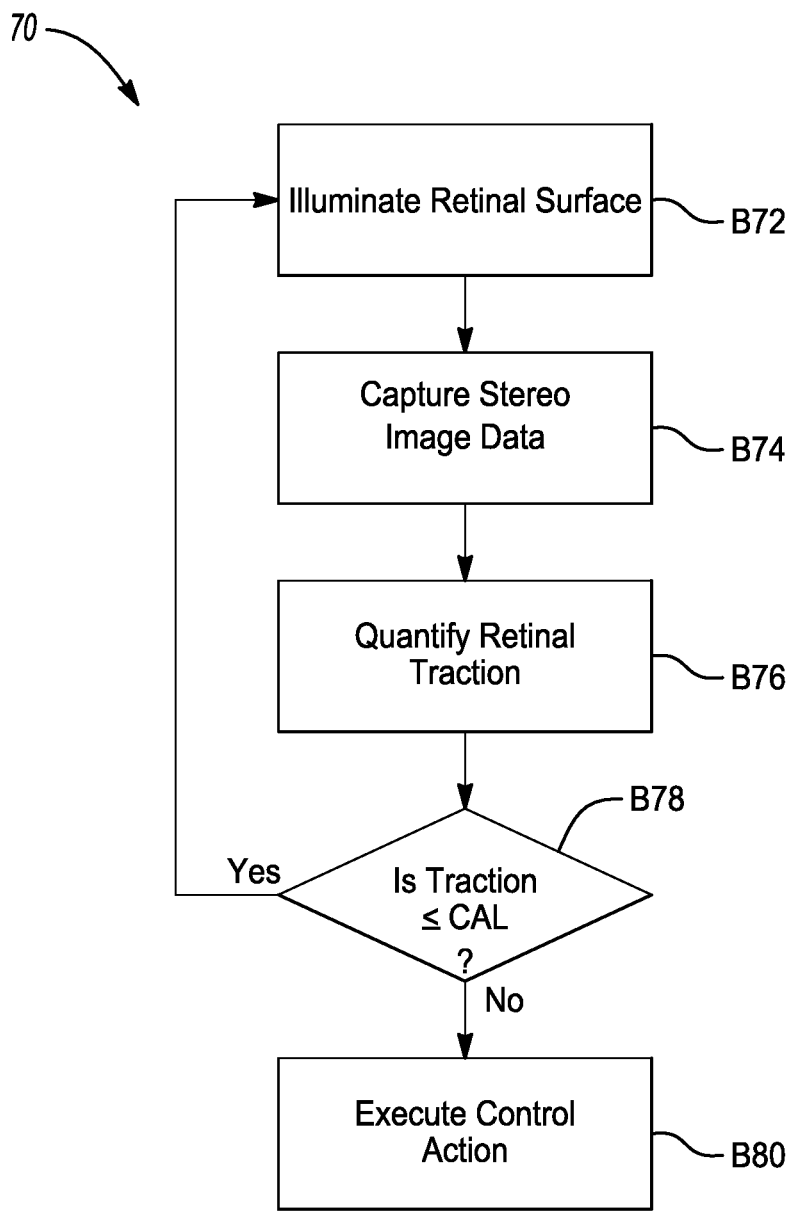
FIG. 6 is a flow chart describing an exemplary method for quantifying and tracking retinal traction using the traction system shown in FIG. 1.

Referring now to FIG. 6, execution of instructions stored or recorded in the memory 54 of the ECU 50 as shown in FIG. 3 causes the CPU 52 and other hardware of the ECU 50 to perform the method 70. A representative embodiment of the method 70 commences with logic block B72, which includes illuminating the retina 25 of FIG. 2, e.g., with directed light LL from the endoilluminator 32 of FIG. 3, along with possibly some additional light from the lamp 17 of FIG. 1. Surgical steps preceding implementation of logic block B72 would include creating an incision in the patient eye 30 of FIG. 3 and carefully inserting the endoilluminator 32 and the surgical tool 34 into the vitreous cavity 15. The method 70 then proceeds to logic block B74.

Logic block B74 of FIG. 6 entails receiving the stereo image data 38 of FIG. 3 from the stereo camera 16 via the ECU 50. This occurs in real-time during the ophthalmic procedure 13. The ECU 50 may be separate from the stereo camera 16 in some embodiments, as depicted for illustrative clarity. Alternatively, the ECU 50 may include the LCP 36 of the stereo camera 16, such that the LCP 36 is integral with the ECU 50, i.e., the ECU 50 and the stereo camera 16 are effectively a single functional unit, thus reducing component count and possibly providing other processing efficiencies and reduced communications latency.

Figure 5:
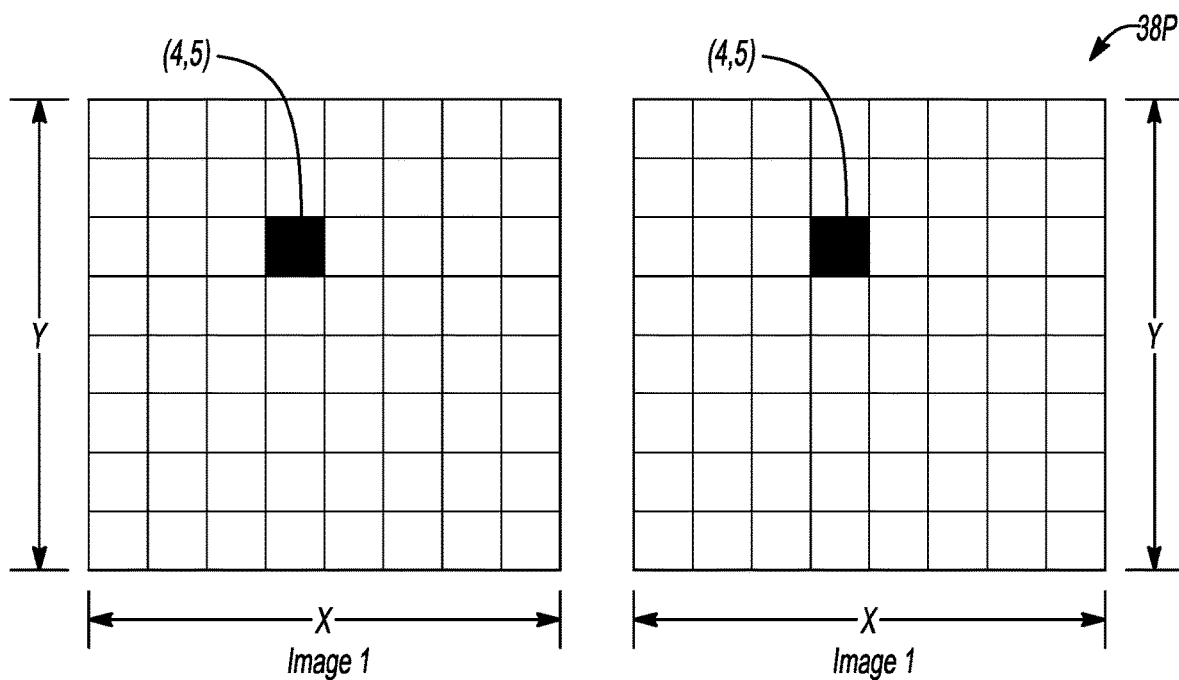
FIG. 5 is a schematic illustration of stereo image data and associated tracking points usable as part of the disclosed solutions.

Referring briefly to FIG. 5, the collected stereo image data 38 is formed in digital embodiments from image pixels, and therefore logic block B74 of FIG. 6 also includes identifying a corresponding pixel field of each of the constituent images of the stereo image pair 38P. For example, Image 1 and Image 2 are shown as 8 pixel by 8 pixel (8×8) digital images arranged in a nominal (X, Y) pixel coordinate system. As Images 1 and 2 are collected at the same instant in time, an assigned pixel (4, 5) in Image 1 coincides with the same pixel (4, 5) in Image 2, and so forth. That is, within a given stereo image pair 38P, pixel (4, 5) of Image 1 coincides with pixel (4, 5) of Image 2. As part of logic block B74 of FIG. 6, the ECU 50 automatically or with the assistance or direction of the surgeon, e.g., via input signals (not shown), assigns tracking points to at least one coinciding pixel within the stereo image pair 38P. Within the scope of the method 70, this action may entail identifying a particular coinciding pixel in each image of the stereo image pair 38P. Or, if a single coinciding pixel provides insufficient resolution for tracking, a defined pixel cluster of such coinciding pixels may be assigned. The method 70 then proceeds to logic block B76.

At logic block B76 of FIG. 6, the ECU 50 shown in FIG. 3 next quantifies retinal traction using the collected stereo image data 38. As part of logic block B76, the ECU 50 may automatically perform the above-noted DIC process to the stereo image pair(s) 38P in the stereo image data 38 in order to ascertain relative motion of the tracking points assigned as part of logic block B74. As understood in the art, DIC is an optical technique used in the digital image processing arts to quantify static or dynamic deformation, contour, strain, vibration, and other displacements in an imaged subject. In the present instance, the imaged subject is the retina 25, the ILM 31 of FIG. 2, and the surrounding intraocular tissue, with correlation applied to the identified tracking points from logic block B74.

Also as part of logic block B76, the ECU 50 also associates the relative motion of such tracking points with retinal traction, as quantified in logic block B74. For example, the ECU 50 may reference the traction map 55 shown schematically in FIG. 3, e.g., as a lookup table indexed by relative motion of the tracking points. A given relative motion value may correspond, for example, to a value referred to herein as a numeric traction quotient, with such a value being indicative of the magnitude of the retinal traction. Such a numeric traction quotient could be normalized in a possible embodiment, with 0 corresponding to no traction on the retina 25 and 1 corresponding to a maximum amount traction. Non-normalized embodiments may be used in the alternative, as may be the actual corresponding traction values.

Motion of the patient eye 30 may occur at times due to patient motion or external forces. For instance, a patient may move during surgery, whether due to the patient's own volition or in response to the surgeon bumping the patient and/or the platform 14 of FIG. 1, or otherwise. The resulting motion is referred to in the art as free-body or solid-body motion. With respect to such motion, the relative distance between two coinciding image pixels or tracking points in the stereo image pair 38P remains the same under motion. The relative motion considered herein for the purpose of quantifying retinal traction thus excludes such baseline solid-body motion, e.g., by applying a solid-body motion filter. This enables the ECU 50 to account for solid-body motion of the retina 25 as part of the DIC process occurring within the scope of logic block B76. The method 70 proceeds to logic block B78 once the ECU 50 has determined the numeric traction quotient.

At logic block B78 of FIG. 6, the ECU 50 next compares the numeric traction quotient from logic block B76 to a calibrated traction threshold ("Is Traction≤CAL?"), or to multiple such traction thresholds corresponding to different regions or zones of the retina 25 as described above. The method 70 repeats logic block B72 when none of the calibrated traction thresholds are exceeded, i.e., when retinal traction is less than or equal to the above-noted calibrated traction threshold(s). The method 70 proceeds in the alternative to logic block B80 when the ECU 50 affirmatively determines that one or more of the calibrated traction thresholds have been exceeded.

Logic block B80 involves executing a control action based on the numeric traction quotient, with the control action being indicative of the retinal traction. For example, the ECU 50 could, in response to the numeric traction quotient exceeding a calibrated traction threshold, activate the indicator device 20A and/or 20B in a suitable manner. In embodiments in which the multi-axis surgical robot 60 of FIG. 3 is used, the control action could include transmitting motion control signals to the surgical robot 60, and in particular to one or more revolute joints thereof as understood in the art, to change a position for force offloading, or in possible autonomous embodiments to change a scraping force, pulling/tugging force, and/or other value as needed in response to the numeric traction quotient.

As part of logic block B80, the ECU 50 may consider the magnitude by which a given traction threshold was exceeded in logic block B78 when determining which of many possible control actions the ECU 50 should execute. That is, the control action could be commensurate with the magnitude of a difference between the current level of retinal traction and the exceeded traction threshold, with the ECU 50 possibly escalating the corresponding alarms as the magnitude increases. Executing the control action may optionally include adjusting a setting of the one or more display screens 20 and/or 200 of FIG. 1 when the numeric traction quotient exceeds a calibrated traction threshold.

An illustrative example includes establishing a corresponding traction threshold for the representative zones Z1 and Z2 of FIG. 4. The ECU 50 could display a color-coded version of the heat map 45 of FIG. 4 via the display screens 20 and/or 200 of FIG. 1, which would enable the surgeon to discern at a glance whether or not too much traction is being applied in a particular zone relative to another. In an embodiment, the ECU 50 could automatically adjust the color and/or brightness of "hotter" zones as retinal traction in a given zone progressively increases, such as by gradually coloring the zone from yellow to red as retinal traction increases. Upon crossing a traction threshold for a given zone, the ECU 50 could activate the indicator device 20B of FIG. 3 in a particular complementary manner, such as by sounding a warning tone, vibrating, displaying a warning message, etc. In lieu of or in addition to such a warning message, the ECU 50 could prompt the surgeon to use a different surgical tool 34, such as by recommending use of a looped scraper instead of forceps, etc.

By using the ECU 50 of FIGS. 1 and 3, the intuitive heat map 45 of FIG. 4, and the method 70 shown in FIG. 6, a surgeon performing the ophthalmic procedure 13 shown in FIG. 3 is made aware, in an intuitive and possibly localized manner if so desired, of the actual level of traction being applied to the retina 25. Because alarms are not triggered unless and until a given threshold has been exceeded, the present approach is minimally intrusive and readily customizable via the calibratable inputs 58 (arrow CAL of FIG. 3) to meet the preferences of a given surgeon.

In terms of such optional customization, it is recognized herein that surgical results are highly dependent upon the individual skillset and techniques employed by a given surgeon. To that end, the ECU 50 of the present disclosure may be configured to present a range of threshold sensitivity options, possibly including using default settings in which a calibrated set of traction thresholds are used for all patients. In some implementations, however, a surgeon may wish to depart from such default settings to properly account for surgical preferences, or to account for different patient-specific/variable parameters such as age, sex, health status such as diabetes, glaucoma, hypertension, etc., previous injuries, diseases, and/or surgeries, past results, and the like. For example, a surgeon in some approaches may be prompted via the ECU 50 to answer a set of questions regarding the patient, including any or all of the above example parameters, with the ECU 50 thereafter recommending or automatically selecting corresponding thresholds to apply in conjunction with the traction map 55.

With respect to threshold adaptation, in addition to customizing use of the method 70 for a given patient and/or surgeon, the traction thresholds may be adjusted over time using historical results. By way of example, it may be determined over time, using historical results of multiple surgeries over many days, months, or years, that particular control actions associated with exceeding one or more traction thresholds may have been unnecessary, or were premature. In such an instance, the ECU 50 may selectively increase the traction thresholds during subsequent surgeries to permit the surgeon, using the surgeon's professional discretion, to employ higher levels of retinal traction when needed, without fear of damaging the ILM 31 or the retina 25. Alternatively, when historical results indicate that the applied traction thresholds are too low, perhaps resulting in damage or unsatisfactory results where none were expected, the ECU 50 may decrease the traction thresholds.

Those skilled in the art will recognize that the method 70 may be implemented as computer-readable instructions, recorded in memory 54 of FIG. 3 or in a separate memory location, with execution of the instructions by the CPU 52 allowing the CPU 52 to quantify retinal traction on the retina 25 of the patient eye 30 shown schematically in FIG. 3. That is, execution of the instructions embodying the method 70 causes a system constructed of the CPU 52 and memory 54 to receive the stereo image data 38 from the stereo camera 16 of FIG. 3 during the ophthalmic procedure 13, and to assign tracking points within the stereo image pair 38P.

Execution of the instructions also causes the CPU 52 to automatically perform the above-described DIC process using the stereo image pair 38P to thereby ascertain relative motion of the tracking points, e.g., as shown in FIG. 5, and to associate relative motion of the tracking points with the retinal traction, using the traction map 55 of FIG. 3, as a numeric traction quotient indicative of magnitude of the retinal traction. The CPU 52, alone or using other associated hardware, then communicates the control signal (arrow $CC_{20A}$) to the indicator device 20A when the numeric traction quotient exceeds one or more calibrated traction thresholds. For instance, the control signal (arrow $CC_{20A}$) could be configured to display the above-described color-coded heat map 45 shown in FIG. 4, thereby intuitively displaying the retinal traction via the display screen 20 and/or 200 of FIG. 1.

The detailed description and the drawings are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims.

Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A tracking system for quantifying retinal traction in a patient eye during an ophthalmic procedure, the tracking system comprising:
   an indicator device;
   a stereo camera configured to collect and output stereo image data of a retina of the patient eye; and
   an electronic control unit (ECU) in communication with the indicator device and the stereo camera, wherein the ECU is configured to:
      receive the stereo image data from the stereo camera during the ophthalmic procedure, the stereo image data including stereo image pairs;
      assign tracking points as coinciding pixels of the stereo image pairs;
      automatically perform a digital image correlation (DIC) process to the stereo image pairs to ascertain relative motion of the tracking points;

associate relative motion of the tracking points with the retinal traction, using a traction map of the ECU, as a numeric traction quotient indicative of magnitude of the retinal traction; and execute a control action based on the numeric traction quotient, wherein the control action is indicative of the retinal traction.

2. The tracking system of claim 1, wherein the stereo camera includes a local control processor that is integral with the ECU.

3. The tracking system of claim 1, wherein as part of the DIC process, the ECU is configured to apply a solid-body motion filter to the relative motion to account for solid-body motion of the retina.

4. The tracking system of claim 1, wherein the indicator device includes one or more high-resolution display screens.

5. The tracking system of claim 4, wherein the ECU is configured to execute the control action based on the numeric traction quotient by adjusting a setting of the one or more high-resolution display screens when the numeric traction quotient exceeds a calibrated traction threshold.

6. The tracking system of claim 5, wherein adjusting the setting of the one or more high-resolution display screens includes displaying a color-coded heat map of the retinal traction via the one or more high-resolution display screens.

7. The tracking system of claim 6, wherein the ECU is configured to display the color-coded heat map of the retinal traction on top of a stereo image formed by the stereo image pairs.

8. The tracking system of claim 1, wherein the ECU is configured to execute the control action in response to the numeric traction quotient exceeding a calibrated traction threshold.

9. The tracking system of claim 8, wherein the ECU is configured to receive calibratable inputs from a user of the tracking system, and to adjust the calibrated traction threshold based on the calibratable inputs.

10. A method for quantifying retinal traction on a retina of a patient eye during an ophthalmic procedure, the method comprising:

receiving, via an electronic control unit (ECU), stereo image data of the retina from a stereo camera during the ophthalmic procedure, wherein the stereo image data includes stereo image pairs;

assigning tracking points as coinciding pixels of the stereo image pairs;

automatically performing a digital image correlation (DIC) process, via the ECU, using the stereo image pairs to thereby ascertain relative motion of the tracking points;

associate relative motion of the tracking points with the retinal traction, using a traction map of the ECU, to thereby determine a numeric traction quotient indicative of magnitude of the retinal traction; and executing a control action via the ECU using an indicator device, based on the numeric traction quotient, wherein the control action is indicative of the retinal traction.

11. The method of claim 10, wherein automatically performing the DIC process includes applying a solid-body motion filter to the relative motion to thereby account for solid-body motion of the retina.

12. The method of claim 10, wherein the indicator device includes one or more display screens, and wherein executing the control action based on the numeric traction quotient includes adjusting a setting of the one or more display screens when the numeric traction quotient exceeds a calibrated traction threshold.

13. The method of claim 12, wherein adjusting the setting includes displaying a color-coded heat map of the retinal traction via the one or more display screens.

14. The method of claim 13, wherein displaying the color-coded heat map of the retinal traction includes displaying the color-coded heat map on top of a stereo image formed from the stereo image pairs.

15. The method of claim 10, wherein executing the control action in response to the numeric traction quotient includes comparing the numeric traction quotient to a calibrated traction threshold, and activating the indicator device when the numeric traction quotient exceeds the calibrated traction threshold.

16. The method of claim 15, further comprising receiving calibratable inputs via the ECU, and thereafter adjusting the calibrated traction threshold based on the calibratable inputs.

17. The method of claim 15, wherein the calibrated traction threshold includes a plurality of calibrated traction thresholds each corresponding to a different zone or region of the retina.

18. The method of claim 17, further comprising adapting the calibrated traction thresholds over time in response to historical data indicative of past surgical results.

19. A system for quantifying retinal traction on a retina of a patient eye, comprising:

a central processing unit (CPU); and computer-readable media on which is recorded instructions, wherein execution of the instructions by the CPU causes the CPU to:

receive stereo image data from a stereo camera during an ophthalmic procedure, the stereo image data including stereo image pairs;

assign tracking points as coinciding pixels within the stereo image pairs;

automatically perform a digital image correlation (DIC) process using the stereo image pairs to thereby ascertain relative motion of the tracking points;

associate relative motion of the tracking points with the retinal traction, using a traction map, as a numeric traction quotient indicative of magnitude of the retinal traction; and communicate a control signal to an external indicator device when the numeric traction quotient exceeds one or more calibrated traction thresholds.

20. The system of claim 19, wherein the external indicator device includes a display screen, and wherein the control signal is configured to display a color-coded heat map of the retinal traction via the display screen.

* * * * *